United States Patent
Soerens

(10) Patent No.: US 7,777,095 B2
(45) Date of Patent: Aug. 17, 2010

(54) BIODEGRADABLE ABSORBENT MATERIAL

(75) Inventor: Dave Allen Soerens, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 313 days.

(21) Appl. No.: 10/880,127

(22) Filed: Jun. 29, 2004

(65) Prior Publication Data

US 2005/0288641 A1    Dec. 29, 2005

(51) Int. Cl.
A61F 13/15    (2006.01)
(52) U.S. Cl. .......... 604/367; 604/368; 524/377
(58) Field of Classification Search .......... 604/367, 604/368, 385.01, 385.02, 385.23; 526/240, 526/317.1; 525/54.1; 524/503, 377, 549
See application file for complete search history.

(56) References Cited

U.S. PATENT DOCUMENTS

| | | | |
|---|---|---|---|
| 5,219,928 A * | 6/1993 | Stofko et al. ............ | 525/57 |
| 5,360,419 A * | 11/1994 | Chen et al. ............ | 604/374 |
| 6,323,388 B1 * | 11/2001 | Melius et al. ............ | 604/368 |
| 6,361,651 B1 | 3/2002 | Sun | |
| 6,387,495 B1 | 5/2002 | Reeves et al. | |
| 6,706,945 B1 * | 3/2004 | Melius et al. ............ | 604/368 |
| 6,844,066 B2 * | 1/2005 | Hamed ............ | 428/393 |
| 2002/0150761 A1 | 10/2002 | Lange et al. | |
| 2004/0058600 A1 * | 3/2004 | Bunyard et al. ............ | 442/59 |
| 2004/0116885 A1 * | 6/2004 | Soerens et al. ............ | 604/378 |

FOREIGN PATENT DOCUMENTS

| | | |
|---|---|---|
| WO | WO 98/24832 A1 | 6/1998 |
| WO | WO 02/096953 | 12/2002 |
| WO | WO 2004/054489 | 7/2004 |
| WO | WO 2005/016393 | 2/2005 |
| WO | WO 2005/025628 | 3/2005 |

OTHER PUBLICATIONS

Neumann, A.W., and R.J. Good, "Techniques of Measuring Contact Angles," Chapter 2 of *Surface and Colloid Science*, vol. 11, Experimental Methods, edited by R.J. Good and R.R. Stromberg, Plenum Press, 1979, pp. 31-91.

Lichstein, Bernard M., "Demand Wettability, A New Method for Measuring Absorbency Characteristics of Fabrics," *INDA Technical Symposium—Nonwoven Product Technology*, Washington, D.C., Mar. 1974, pp. 129-142.

* cited by examiner

*Primary Examiner*—Tatyana Zalukaeva
*Assistant Examiner*—Lynne Anderson
(74) *Attorney, Agent, or Firm*—Denise L. Stoker; Bryan R. Rosiejka

(57) ABSTRACT

An absorbent composition having a biodegradable absorbent polymer and a hydrophilic soft polymer surface modifying agent. The absorbent composition exhibits improved absorbency under load and gel bed permeability when subjected to an Absorbency Under Load Test and a Gel Bed Permeability Test, respectively. The absorbent composition can be made by combining a biodegradable absorbent polymer with an aqueous solution of a hydrophilic soft polymer and then drying the biodegradable absorbent polymer.

15 Claims, 2 Drawing Sheets

BIODEGRADABLE ABSORBENT MATERIAL

BACKGROUND

Disposable absorbent articles are useful for absorbing many types of fluids, including fluids secreted or eliminated by the human body. Superabsorbent materials are frequently used in disposable absorbent articles to help improve the absorbent properties of such articles. Superabsorbent materials are generally polymer based and are available in many forms, such as powders, granules, microparticles, films and fibers. Upon contact with fluids, superabsorbent materials swell by absorbing fluid into their structure. The superabsorbent materials quickly absorb fluids insulted into the articles and retain such fluids to prevent leakage and provide a dry feel even after fluid insult.

In general, superabsorbent materials are water-insoluble, and although they can absorb many times their weight in fluids, they are relatively resistant to biodegradation. As a result, a separate class of superabsorbent materials has been developed which focuses on biodegradation, known in the art as biodegradable superabsorbents, or "bioSAP's." Unlike conventional polyacrylate superabsorbents, bioSAP's become biodegradable over time under conditions that promote microbial growth.

Certain biodegradable superabsorbent materials, such as those composed of crosslinked polysaccharides, tend to exhibit lower absorbency properties, particularly absorbency under load and gel bed permeability, versus conventional non-biodegradable polyacrylate superabsorbents. Thus, it is desirable in the art to improve the absorbency properties of such biodegradable superabsorbent absorbent materials. However, increasing one of these properties typically leads to a reduction in the other property. For example, attempts to increase absorbency capacity in such bioSAP's can result in sloppy gels with significantly reduced permeability. Similarly, attempts to improve permeability can result in a significant reduction in absorbency under load. Therefore, there is a need for biodegradable superabsorbents having high gel bed permeability and absorbency under load.

SUMMARY

This invention is directed to biodegradable absorbent materials with good fluid handling properties. The invention is further directed to biodegradable superabsorbent materials having increased permeability and absorbency under load. The invention is even further directed to absorbent articles comprising such materials and method of making the same.

The biodegradable superabsorbent material of the present invention is comprised of a suitable biodegradable superabsorbent base material having crosslinked polysaccharides which exhibits an increase in both gel bed permeability and absorbency under load after being treated with an aqueous solution of a hydrophilic soft polymer. In one example, the biodegradable superabsorbent base material is carboxymethyl cellulose based.

In one embodiment, the hydrophilic soft polymer is a cationic polymer. The cationic polymer can have functional groups consisting of primary, secondary, and tertiary amine, imine, quaternary ammonium, as well as combinations of these. Suitably, the cationic polymer includes about 0.1-percent to about 20-percent by mass ester units which include alkoxysilane functionality, such as methacryl esters which contain an alkoxysilane group or acryl esters which contain an alkoxysilane group. Examples of suitable ester units include acrylate and methacrylate ester units. Upon exposure to water, the alkoxysilane functionality forms a silanol group which condenses to form a crosslinked polymer. Suitably, the soft polymer has a glass transition temperature below about twenty degrees Celsius. Examples of suitable cationic polymers for the present invention include salts of polyvinyl amine, polydiallyl dimethyl ammonium, polyacrylamidopropyl trimethyl ammonium, polyamino propanol vinyl ether, polyallylamine, acryloyloxyethyl-trialkyl-substituted ammonium, acryloyloxypropyl-trialkyl-substituted ammonium, acrylamidoethyl-trialkyl-substituted ammonium, acrylamidopropyl-trialkyl-substituted ammonium. Suitable counter ions to the cationic ammonium polymers include, but are not limited to, chloride, hydroxide, and methyl sulfonate.

One method of treating the suitable biodegradable superabsorbent material involves adding the aqueous solution to the superabsorbent material, mixing the aqueous solution with the superabsorbent material, and drying the treated superabsorbent material. The hydrophilic soft polymer is suitably present in the aqueous solution in an amount between about 0.1-percent and about 10-percent by weight of the aqueous solution. The superabsorbent material may be treated with 10-percent to about 1000-percent aqueous solution by weight of the superabsorbent material. Additionally, the superabsorbent material may tend to agglomerate during or subsequent to treatment, in which case an additional step of separating and breaking up the agglomerated structures should be performed.

The improved biodegradable superabsorbent material of the present invention can be utilized in numerous applications, such as in disposable absorbent articles. Such absorbent articles include, but are not limited to, infant diapers, child training pants, adult incontinence products, feminine care products, wound dressings, paper towels, tissues, and the like. The superabsorbent material may also be used as part of a component of such absorbent articles, such as in an absorbent core or other absorbent layer, and could be located in a region of the layer having a concentration of about 10-percent or greater of the superabsorbent material of the present invention based on total weight of the absorbent layer.

DEFINITIONS

Figure 1:
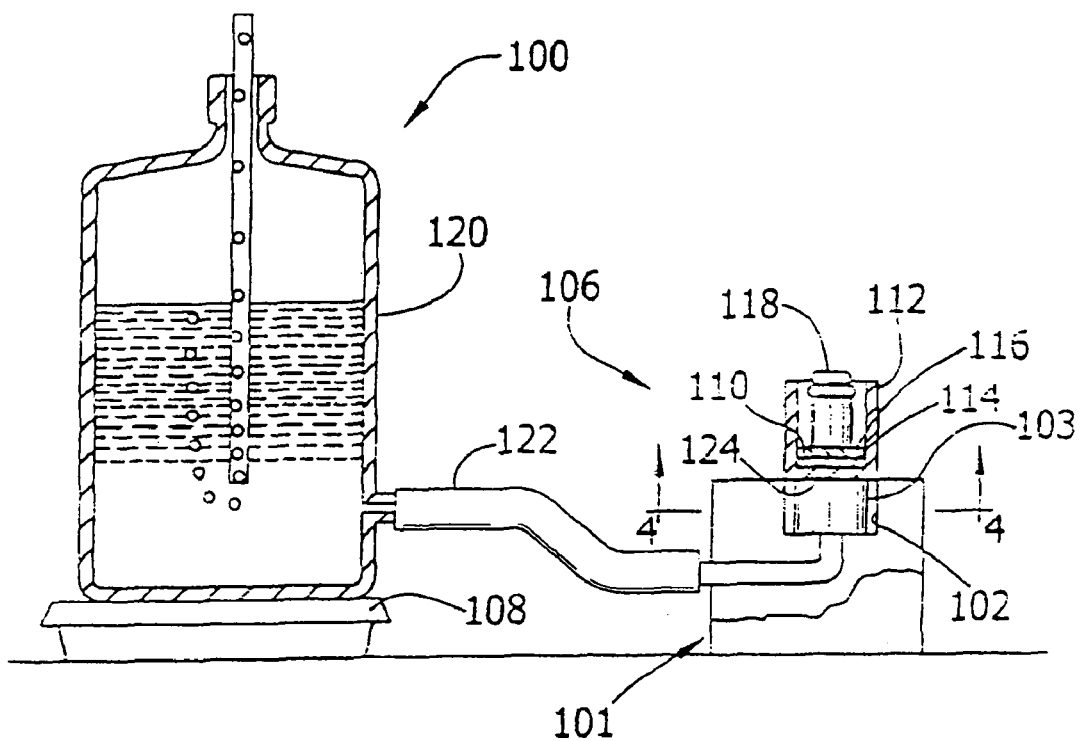
FIG. 1 depicts apparatus used to measure absorbency under load (AUL) of free-flowing particles.

When introducing elements of the present invention or the preferred embodiment(s) thereof, the articles "a", "an", "the" and "said" are intended to mean that there are one or more of the elements. When employed in the present disclosure, the terms "comprises," "comprising," "including" and "having," and other derivatives from the root terms "comprise," "include" and "have" are intended to be open-ended terms that specify the presence of any stated features, elements, integers, steps, or components, and are not intended to preclude the presence or addition of one or more other features, elements, integers, steps, components, or groups thereof.

As used herein, the term "absorbent article" includes personal care absorbent articles such as diapers, training pants, swim wear, absorbent underpants, adult incontinence products, feminine hygiene products, and the like, as well as absorbent wiping articles such as facial tissue, paper towels, kitchen towels, away-from-home towels, wet-wipes, and the like, as well as medical absorbent articles such as medical absorbent garments, drapes, gowns, bandages, masks, wound dressings, underpads, wipes, and the like.

As used herein, the term "hydrophilic" refers to a material having a contact angle of water in air of less than 90 degrees. For purposes of this application, contact angle measurements are determined as set forth in "Surface and Colloid Science—Experimental Methods," Vol. II, Robert J. Good and Robert J. Stromberg, Ed. (Plenum Press, 1979).

As used herein, the term "hydrophilic soft polymer" refers to a material that results from the polymerization of water-soluble monomers with alkyl chains of 3 carbons or less, and having a glass transition temperature (Tg) of less than 20 degrees Celsius for the dried polymer. Hydrophilic soft polymers act as an elastomer at room temperature and are capable of rapid, nonradiative crosslinking.

The terms "particle," "particles," "particulate," "particulates" and the like, mean that the material is generally in the form of discrete units. The units can comprise granules, powders, spheres, pulverized materials or the like, as well as combinations thereof. The particles can have any desired shape such as, for example, cubic, rod-like, polyhedral, spherical or semi-spherical, rounded or semi-rounded, angular, irregular, etc. Shapes having a large greatest dimension/smallest dimension ratio, like needles, flakes and fibers, are also contemplated for inclusion herein. The terms "particle" or "particulate" may also include an agglomeration comprising more than one individual particle, particulate or the like. Additionally, a particle, particulate or any desired agglomeration thereof may be composed of more than one type of material.

As used herein, the term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to, isotactic, syndiotactic and atactic symmetries.

As used herein, the term "pre-screened," as used herein, refers to a sample of superabsorbent material that has been screened or otherwise sorted to include particles within a specified size range. Unless otherwise stated herein, the pre-screened superabsorbent materials include particles in a size ranging from 300 to 600 microns. A more detailed description of the screening process is provided below in the Average Particle Size Distribution Test Method.

As used herein, the term "superabsorbent" refers to a water-swellable, water-insoluble organic or inorganic material capable, under the most favorable conditions, of absorbing at least about 15 times its weight and, more desirably, at least about 25 times its weight in an aqueous solution containing 0.9 weight percent sodium chloride. The superabsorbent materials can be natural, synthetic, and modified natural polymers and materials. In addition, the superabsorbent materials can be inorganic materials, such as silica gels, or organic compounds such as crosslinked polymers. The superabsorbent material may be biodegradable or non-biodegradable. The superabsorbent materials can include particles, fibers, tows, flakes, films, foams, and the like. A material is "absorbent" if it absorbs at least five times its weight of the aqueous solution under these conditions.

As used herein, the term "un-screened" is used interchangeably with the term "as-is." These terms refer to a sample of superabsorbent material that has not been screened or otherwise sorted to include only particles within a specified size range. Instead, un-screened superabsorbent material may include particles of any size, such as particles that have undergone changes in size and shape as a result of mechanical damage.

These terms may be defined with additional language in the remaining portions of the specification.

DETAILED DESCRIPTION

This invention is directed to biodegradable absorbent materials with good fluid handling properties. The invention is further directed to biodegradable superabsorbent materials having increased permeability and absorbency under load. The invention is even further directed to absorbent articles comprising such materials and method of making the same.

In general, biodegradable superabsorbents exhibit absorbency properties that are inferior to conventional superabsorbent materials, such as polyacrylates. Biodegradable superabsorbents exhibit an AUL value (under 0.3 psi load) of less than 20 grams of 0.9 weight percent sodium chloride aqueous solution per gram of the polymer or superabsorbent and a gel bed permeability (GBP) value under 0 psi swell pressure measured on 300-600 micron particles less than about 100 ($\times 10-9$ cm2), or less than 50 ($\times 10-9$ cm2), or less than 10 ($\times 10-9$ cm2). Moreover, biodegradable superabsorbent materials, to a greater degree than conventional superabsorbent materials, tend to exhibit a somewhat inverse effect with regard to absorbent properties. For example, when one increases permeability, the absorbency under load typically decreases significantly.

In contrast, suitable biodegradable superabsorbent materials of the invention include biodegradable superabsorbent base materials which, after treatment, exhibit an increase in both absorbency under load and permeability, as measured by the Absorbency Under Load Test and the Gel Bed Permeability Test respectively, described in detail in the Examples below. One example of a biodegradable superabsorbent material of the present invention has at least a portion of its surface crosslinked and is coated with a hydrophilic soft polymer. In another example, the biodegradable superabsorbent base material is carboxymethyl cellulose based. In another example, the base material is a surface crosslinked polycarboxy polysaccharide. One suitable superabsorbent base material is W106253, available from Stockhausen GmbH & Co. KG, a business having offices located in Greensboro, N.C., U.S.A. The base material can include particles, fibers, tows, flakes, films, foams, and the like.

Unlike typical biodegradable superabsorbent materials, the treated biodegradable superabsorbent materials of the invention exhibit an absorbency under 0.3 psi load (AUL) of at least 20 grams of 0.9 weight percent sodium chloride aqueous solution per gram of the polymer or superabsorbent and a gel bed permeability (GBP) value under 0 psi swell pressure measured on 300-600 micron particles of at least about 100 ($\times 10-9$ cm2), such as at least 200 ($\times 10-9$ cm2), or at least 300 ($\times 10-9$ cm2). The biodegradable superabsorbent materials of the disclosure further have an absorbency under 0.9 psi load (AUL) of at least 13 grams of 0.9 weight percent sodium chloride aqueous solution per gram of the polymer or superabsorbent and a gel bed permeability (GBP) value under 0.3 psi swell pressure measured on 300-600 micron particles of at least about 20 ($\times 10-9$ cm2), or at least 50 ($\times 10-9$ cm2), or at least 100 ($\times 10-9$ cm2).

Both the permeability and the absorbency under load of the superabsorbent material can be increased by treating the superabsorbent material with an aqueous solution. A suitable aqueous solution comprises a hydrophilic soft polymer that can be crosslinked. The hydrophilic soft polymer is suitably a cationic polymer. The cationic polymer can have functional groups consisting of primary, secondary, and tertiary amine, imine, quaternary ammonium, as well as combinations of these. In one embodiment, the cationic polymer includes about 0.1-percent to about 20-percent by mass ester units which include alkoxysilane functionality. Examples of suitable ester units include acrylate and methacrylate ester units. Upon exposure to water, the alkoxysilane functionality forms a silanol group which condenses to form a crosslinked polymer.

The hydrophilic soft polymers of the invention have a glass transition temperature (Tg) of about 20 degrees Celsius or less, such as about 10 degrees Celsius or less, or about 0 degree Celsius or less. In general, a lower glass transition temperature corresponds to a softer polymer. Examples of suitable cationic polymers for the aqueous treatment solution include salts of polyvinyl amine, polydiallyl dimethyl ammonium acryloyloxyethyl-trialkyl-substituted ammonium, acryloyloxypropyl-trialkyl-substituted ammonium, acrylamidoethyl-trialkyl-substituted ammonium, acrylamidopropyl-trialkyl-substituted ammonium and copolymers or mixtures of these. Suitable counter ions to the cationic ammonium polymers include, but are not limited to chloride, hydroxide, methyl sulfonated.

One method of treating the biodegradable superabsorbent base material to increase both the absorbency under load and the gel bed permeability involves adding the hydrophilic soft polymer to the superabsorbent material, mixing the polymer with the superabsorbent material, and then drying the treated superabsorbent material. The hydrophilic soft polymer is suitably in an aqueous solution, present in an amount between about 0.1-percent and about 10-percent by weight of the solution, such as between about 0.5-percent and about 15-percent, or between about 2-percent and about 10-percent.

The aqueous solution can be added to the superabsorbent base material in an amount between about 10-percent and about 1000-percent, such as between about 50-percent and about 800-percent, or between about 100-percent and about 500-percent by weight of the superabsorbent material. The aqueous solution and the superabsorbent material are then mixed together. The mixing can be accomplished using any number of methods known in the art. In one example, the mixing is accomplished by stirring with a spatula to distribute the coating solution and partially swell the superabsorbent material. Potential commercial processes for treating biodegradable superabsorbent include spray drying superabsorbent particles or application of the hydrophilic soft polymer to the ground superabsorbent gel prior to final drying. The resulting biodegradable superabsorbent materials comprise about 5-percent to about 15-percent by weight the hydrophilic soft polymer based on the weight of the superabsorbent materials prior to treatment.

To ensure a uniform surface coating, the mixture of aqueous solution and superabsorbent base material can be stirred for about 0.1 to about 10 minutes. After the aqueous solution has been added to the superabsorbent material, the superabsorbent material can be dried, suitably at a temperature between about 20 and about 150 degrees Celsius, such as between about 50 and about 100 degrees Celsius, for a period of about 0.1 to about 30 hours. The treated superabsorbent material can be dried using any suitable technique known in the art. One such technique is hot air drying.

The process of treating the superabsorbent base material can often result in agglomerating several particles together to form larger than desired agglomerates. Once dried, the treated superabsorbent material can be screened through a sieve to separate any such agglomerates. The agglomerates can then be broken apart using any suitable means known in the art. For example, agglomerated particles can be separated by pressing with one's hand or by using equipment capable of providing gentle pressing and kneading. Other methods may be employed to break apart the agglomerated particles, such as those that minimize damaging the superabsorbent material or altering absorbent properties in a negative manner.

A more uniform coating, which contributes to absorbency under load, may be achieved by crosslinking the hydrophilic soft polymers after they have been coated onto the superabsorbent materials. A beneficial mechanism to achieve crosslinking after surface treatment is to use a modified hydrophilic soft polymer which is self-crosslinkable. Such self-crosslinkable latent crosslinkers include about 0.1-percent to about 20-percent by mass acrylate ester units or methacrylate ester units, which include an alkoxysilane functionality. Upon exposure to water, the alkoxysilane functionality forms a silanol group which condenses to form a crosslinked polymer.

An example of a self-crosslinking hydrophilic soft polymer may also comprise about 0.1-percent to about 75-percent by mass polyolefin glycol and/or polyolefin oxide units. The polyolefin glycol and/or oxide may include an alpha-olefin having about 2 to about 4 carbon atoms, and may include about 30 to about 15,000 olefin glycol and/or oxide units per molecule. The polyolefin glycol and/or oxide may be graft polymerized with the acrylate or methacrylate ester to form a graft copolymer. The polyolefin glycol and/or oxide may be a homopolymer or copolymer. The polyolefin glycol and/or oxide may be a block copolymer including olefin glycol or oxide units having different numbers of carbon atoms, for instance, block copolymers of ethylene oxide and propylene oxide. The polyolefin glycol and/or oxide provide the hydrophilic soft polymer with enhanced flexibility.

The hydrophilic soft polymer can be prepared using a template polymerization process by which the monoethylenically unsaturated polymer and acrylate or methacrylate ester are polymerized in the presence of a pre-formed template polymer, namely the polyolefin glycol and/or polyolefin oxide. The polymerization can be carried out by reacting two different monoethylenically unsaturated monomers, one of which contains an alkoxysilane functionality. The polymerization may be induced by heat, radiation, redox chemical reactions, and other techniques. Suitable radiation initiators include, without limitation, ultraviolet, microwave, and electron beam radiation. The initiator generates free radicals to cause copolymerization of the monomers. In one embodiment, the polymerization reaction is carried out in an organic solvent such as ethanol. The polymerization may also occur in an aqueous solution, or in a combined aqueous and organic solvent.

The polyolefin glycol and/or oxide may or may not be graft polymerized onto the acrylate or methacrylate units during the polymerization process. The resulting hydrophilic soft polymer may contain the polyolefin glycol and/or oxide as a separate component, or as part of the copolymer, or a combination of both.

The resulting polymer has latent moisture-induced crosslinking capability due to the alkoxysilane functionality. This polymer may be applied in a flowable state to a substrate or other end use application. Moisture-induced crosslinking may be accomplished through hydrolysis of the alkoxysilane and subsequent condensation upon removal of the solvent from the substrate, such as by evaporation of the solvent from the substrate or using any other effective technique. Alternatively, hydrolysis of the alkoxysilane and subsequent condensation may occur after solvent removal by exposure of the coating to moisture in ambient air.

The above method is capable of increasing the permeability and absorbency under load of suitable biodegradable superabsorbent materials, as evidenced by an increase in gel bed permeability (GBP) of prescreened or un-screened particles under 0 psi swell pressure (free swell) and at 0.3 psi swell pressure, as well as an increase in absorbency under load (AUL) under 0.3 psi and 0.9 psi. The treatment methods of the invention can be carried out, wholly or in part, as part of the superabsorbent manufacturing process, or any other time prior to or subsequent to incorporating the superabsorbent material into an absorbent article, or even during the absorbent structure, material, or article manufacturing process.

The biodegradable superabsorbent material of the present invention can be utilized in numerous applications. For example, the superabsorbent materials of the invention can be incorporated into, or formed into, any suitable absorbent structures, such as cores, layers, or articles. Suitable absorbent structures include, but are not limited to, homogeneous or heterogeneous mixtures of superabsorbent materials and fibers including natural and/or synthetic fibers, structures comprising layer(s) or discreet pockets of superabsorbent materials adjacent to layer(s) of fibers or nonwoven materials, foams, in-situ polymerization structures, and the like. Examples of suitable absorbent articles include, but are not limited to, personal care products such as diapers, training pants, swim wear, absorbent underpants, adult incontinence products, feminine hygiene products, and the like, as well as absorbent wiping articles such as facial tissue, paper towels, kitchen towels, away-from-home towels, wet-wipes, cleaning devices, and the like, as well as medical absorbent articles such as medical absorbent garments, drapes, gowns, bandages, masks, wound dressings, underpads, wipes, and the like. For example, the absorbent article may include components such as an absorbent core or absorbent layer made up of, or including, at least one region containing at least about 10-percent, such as about 40-percent, or at least about 60-percent, or at least about 80-percent by weight treated superabsorbent material, based on total weight of the absorbent layer. The absorbent layer may also include fibers, functional additives or surfactants, and the like. The absorbent layer may be wrapped within a tissue layer or other suitable wrap material, but for purposes of calculating the composition of the absorbent layer, the absorbent layer does not include the wrap layer.

EXAMPLES

Preparation of Coating Polymer

In this Example, an aqueous hydrophilic soft polymer solution containing acrylate quaternary amine homopolymer was used. A method of making this polymer is listed below.

Two monomer solutions were prepared separately. Solution 1 was prepared as follows. To 48.4 grams of an 80-percent solution of 2-(acryloyoxy)ethyl-trimethylammonium chloride (0.20 moles) was added 25.3 grams of deionized water, and 6.0 grams of PEG 200 (molecular weight 200). Then, 0.18 grams ($1.02 \times 10^{-3}$ moles) of ascorbic acid were added to the solution. This mixture was stirred with a magnetic stir bar at about 60 rpm in a bath of water at about 23 degrees Celsius until the ascorbic acid was dissolved.

Solution 2 was prepared as follows. To 48.4 grams of an 80-percent solution of 2-(acryloyloxy)ethyl-trimethylammonium chloride (0.20 moles) were added 25.3 grams of deionized water, and 6.0 grams of PEG 200 (molecular weight 200), 0.37 ml of 30-percent aqueous hydrogen peroxide and 1.0 ml ($5.42 \times 10^{-3}$ moles) of 3-(trimethoxysilyl)propyl methacrylate. This mixture was stirred with a magnetic stir bar at about 60 rpm in a bath of water at about 23 degrees Celsius to provide a clear solution.

Solution 2 was added to Solution 1 in a water bath at a temperature of 35 degrees Celsius. A thermocouple was used to monitor the temperature and observe the reaction exotherm. Within 6 minutes after the solutions were combined an exotherm was evident by a rise in temperature to 90 degrees Celsius over a period of 3 minutes and the solution became highly viscous. The reaction beaker was removed from the water bath after 60 minutes from the addition of Solution 2 to Solution. 1. Then, 150 grams of deionized water were added to reduce the polymer concentration to about 25-percent.

Coating Procedure 100 grams of the 10-percent coating polymer solution was diluted to 500 grams to make a 2-percent solution. To this solution was added 100 grams of W106253 biodegradable superabsorbent base material, available from Stockhausen GmbH & Co. KG, a business having offices located in Greensboro, N.C., U.S.A. The mixture was stirred with a spatula to distribute the coating solution and partially swell the superabsorbent material. The coated superabsorbent material was spread out on a tray and dried overnight in an oven at 80 degrees Celsius. The dried, treated superabsorbent material was pressed with a glass beaker to break up the agglomerates, and then sieved to obtain particles in the 300 to 600 micron size range.

Results

The coated biodegradable superabsorbent material and an uncoated sample of the W106253 were tested for absorbency under load (AUL) and gel bed permeability (GBP) according the methods described below. Table 1 displays the results.

TABLE 1

| Sample | 0.3 psi AUL g/g | 0.9 psi AUL g/g | 0.0 psi (Free Swell) GBP ($\times 10^{-9}$) $cm^2$ | 0.3 psi GBP ($\times 10^{-9}$) $cm^2$ |
|---|---|---|---|---|
| Untreated W106253 | 18.7 | 10.8 | 5 | 0 |
| Treated W106253 | 22.4 | 13.8 | 329 | 132 |
| % Improvement | 20% | 28% | 7.052% | infinity |

It can be seen that both the absorbency under load and the gel bed permeability increased as a result of the treatment.

Test Methods

Absorbency Under Load Test

The Absorbency Under Load (AUL) Test measures the ability of the superabsorbent material to absorb a 0.9 weight percent solution of sodium chloride in distilled water at room temperature (test solution) while the material is under a load such as 0.3 psi or 0.9 psi. Apparatus 106 for conducting the AUL Test is shown in FIG. 1 and comprises a Demand Absorbency Tester (DAT), generally indicated at 100, which is similar to the Gravimetric Absorbency Test System (GATS) available from M/K Systems of Danners, Mass., U.S.A., and to the system described by Lichstein at pages 129-142 of the INDA Technological Symposium Proceedings, March 1974.

Figure 2:
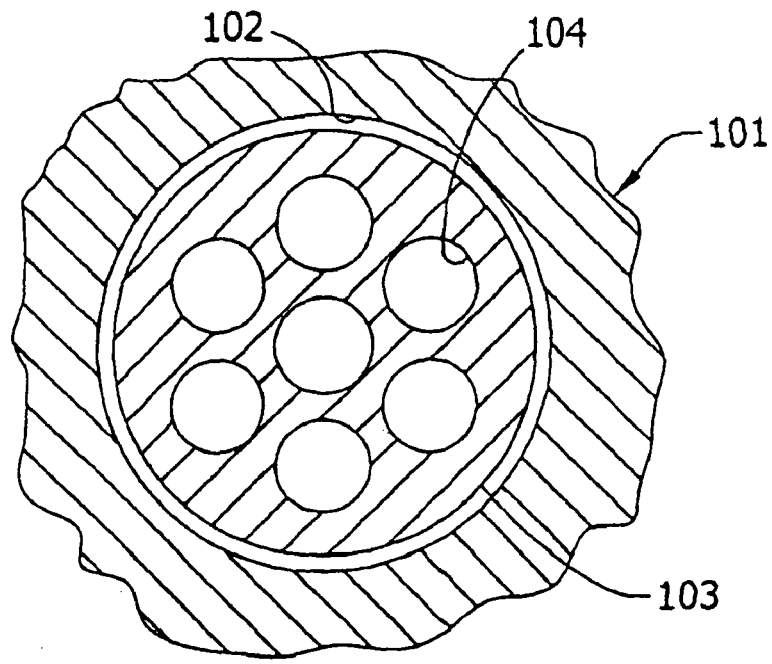
FIG. 2 depicts a bottom view of the apparatus of FIG. 1.

The test apparatus further comprises a test stand, generally indicated at 101 (FIG. 2) having a cavity 102 formed therein and a porous plate 103 seated in the cavity and having a central porous area of about 2.54 cm diameter formed by a plurality of bores 104 extending through the plate. The cavity 102 shown in FIG. 2 has a diameter of about 3.2 cm and the porous plate 103 has a diameter of about 3.1 cm and comprises seven bores 104, each having a diameter of about 0.3 cm. One of the bores 104 is centrally located and the remaining six bores are concentrically positioned about the central bore with the spacing from the center of the central bore to the center of each adjacent bore being about one centimeter.

A sample container for containing a sample 110 to be tested includes a cylinder 112 and a stainless steel cloth screen 114 that is biaxially stretched to tautness and attached to the lower end of the cylinder. The cylinder 112 may be bored from a transparent LEXAN rod or equivalent material, or it may be cut from LEXAN tubing or equivalent material, and has an inner diameter of about one inch (about 2.54 cm). The stainless steel cloth screen 114 is suitably a 100 mesh screen.

A disc, or piston 116 is machined from a LEXAN rod, Plexiglass or equivalent material and has a diameter sized such that it fits within the cylinder 112 with minimum wall clearance but still slides freely. The height of the piston 116 is approximately 0.8 cm and the weight of the piston is suitably about 4.4 grams to provide a load over the cross-sectional area of the sample in the container of about 0.01 psi. A weight 118 is sized (e.g., having a diameter of about 2.5 cm) for seating on the piston 116 to increase the load (e.g., in addition to the weight of the piston) on the sample. For example, a weight of about 100 grams is used to provide a load (including the piston weight) of about 0.3 psi over the cross-sectional area of the sample in the container. In another example, a load of 0.9 psi will have a weight of 300 grams (including the piston weight).

The cavity 102 and the porous plate 103 are in fluid communication with a reservoir 120 containing test solution (0.9 weight percent sodium chloride solution in distilled water at room temperature) via a suitable conduit 122. As shown in FIG. 1, the reservoir 120 is seated on an electrostatic balance 108.

A sample 110 of gel particles weighing about 0.160 grams is prepared by screening the particles through a U.S. standard 30 mesh screen and retaining the particles on a U.S. standard 50 mesh screen so that the sample comprises particles in the size range of about 300 to about 600 microns. The sample is weighed on suitable weighing paper and then loaded into the sample container (with the piston 116 removed) so that the particles are uniformly distributed and overlay the screen at the bottom of the container. The sample container is gently tapped to level the bed of particles in the container.

The AUL Test is initiated by adjusting the level of fluid in the reservoir to the surface of the porous plate, placing a circular piece of GF/A glass filter paper 124 onto the porous plate 103 over the bores 104 formed therein and allowing to become saturated by test solution delivered from the reservoir 120 to the porous plate via the conduit 122. The paper 124 is suitably sized larger than the inner diameter of the cylinder 112 and smaller than the outer diameter thereof to ensure good contact while inhibiting evaporation over the bores 104. The electrostatic balance 108 is zeroed at this time. The piston 116 and weight 118 are placed on the sample within the container and the container (with the sample, piston and weight therein) is placed on the plate 103 over the saturated glass filter paper 124 to allow test solution to be taken into the sample in the container via the conduit 122, bores 104 in the plate 102 and the filter paper.

The electrostatic balance 108 is used to measure the flow of test solution to the sample over a period of about 60 minutes. The amount (in grams) of solution taken into the sample after about 60 minutes divided by the dry weight of the sample (e.g., about 0.160 grams) is the AUL value of the sample in grams of liquid per gram weight of the sample.

Two checks can be made to ensure the accuracy of the measurement. First, the height the piston 116 rises above the screen 114 at the bottom of the sample container multiplied by the cross-sectional area of the piston should roughly equal the amount of solution picked up by the sample over the 60 minute period. Second, the sample container can be weighed before (e.g., while the superabsorbent material is dry) and after the test and the difference in weight should roughly equal the amount of solution picked up by the sample over the 60 minute period.

A minimum of three tests is performed and the results are averaged to determine the AUL value under 0.3 psi load and 0.9 psi load. The samples are tested at 23±1 degrees Celsius at 50±2 percent relative humidity.

Gel Bed Permeability (GBP) Under 0 Psi Swell Pressure Test

Figure 3:
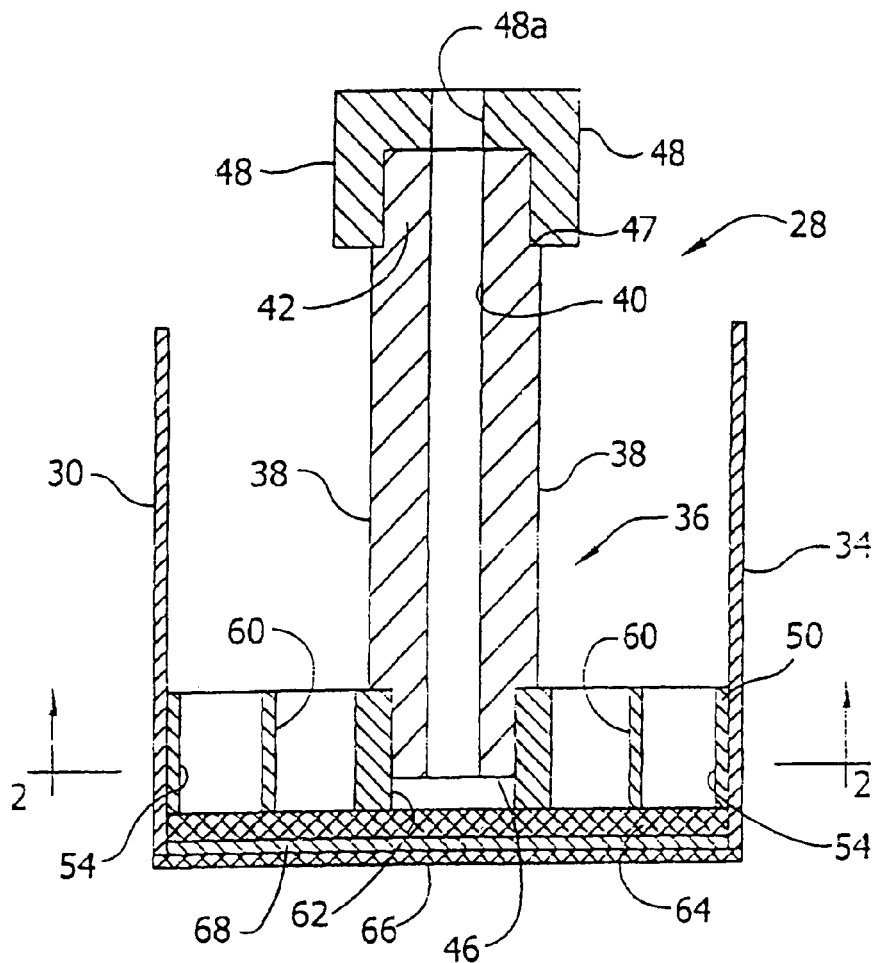
FIG. 3 depicts apparatus used to measure permeability of free-flowing particles.
Figure 4:
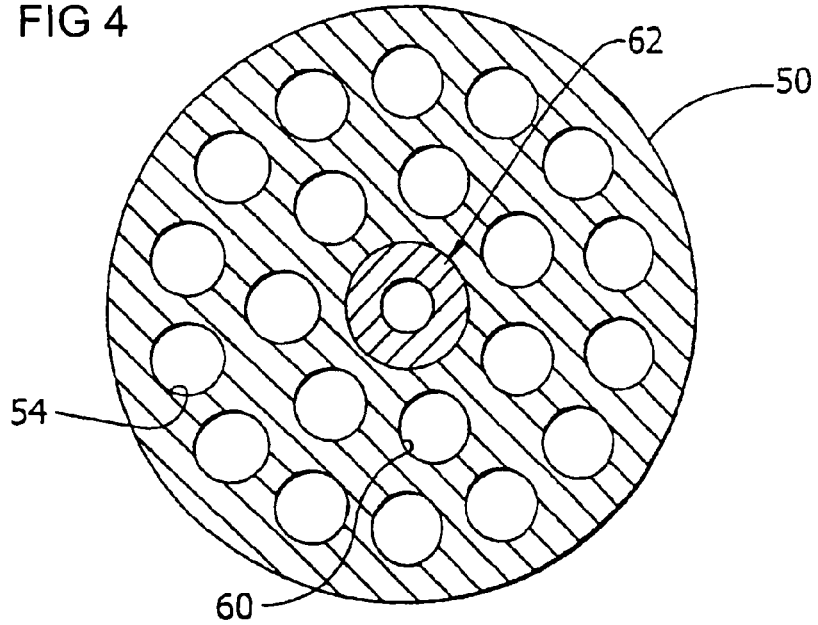
FIG. 4 depicts a bottom view of the apparatus of FIG. 3.

As used herein, the Gel Bed Permeability (GBP) under 0 psi swell pressure test determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIG. 3 and FIG. 4 and indicated generally at 28. The test apparatus 28 comprises a sample container, generally indicated at 30, and a piston, generally indicated at 36. The piston 36 comprises a cylindrical LEXAN shaft 38 having a concentric cylindrical hole 40 bored down the longitudinal axis of the shaft. Both ends of the shaft 38 are machined to provide upper and lower ends respectively, designated 42 and 46. A weight, indicated as 48, rests on one end 42 and has a cylindrical hole 48a bored through at least a portion of its center.

A circular piston head 50 is positioned on the other end 46 and is provided with a concentric inner ring of seven holes 60, each having a diameter of about 0.95 cm, and a concentric outer ring of fourteen holes 54, also each having a diameter of about 0.95 cm. The holes 54, 60 are bored from the top to the bottom of the piston head 50. The piston head 50 also has a cylindrical hole 62 bored in the center thereof to receive end 46 of the shaft 38. The bottom of the piston head 50 may also be covered with a biaxially stretched 100 mesh stainless steel screen 64.

The sample container 30 comprises a cylinder 34 and a 400 mesh stainless steel cloth screen 66 that is biaxially stretched to tautness and attached to the lower end of the cylinder. A gel particle sample, indicated as 68 in FIG. 3, is supported on the screen 66 within the cylinder 34 during testing.

The cylinder 34 may be bored from a transparent LEXAN rod or equivalent material, or it may be cut from a LEXAN tubing or equivalent material, and has an inner diameter of about 6 cm (e.g., a cross-sectional area of about 28.27 $cm^2$), a wall thickness of about 0.5 cm and a height of approximately 10 cm. Drainage holes (not shown) are formed in the sidewall of the cylinder 34 at a height of approximately 7.8 cm above the screen 66 to allow liquid to drain from the cylinder to thereby maintain a fluid level in the sample container at approximately 7.8 cm above the screen 66. The piston head 50 is machined from a LEXAN rod or equivalent material and has a height of approximately 16 mm and a diameter sized such that it fits within the cylinder 34 with minimum wall clearance but still slides freely. The shaft 38 is machined from a LEXAN rod or equivalent material and has an outer diameter of about 2.22 cm and an inner diameter of about 0.64 cm.

The shaft upper end 42 is approximately 2.54 cm long and approximately 1.58 cm in diameter, forming an annular shoulder 47 to support the weight 48. The annular weight 48 has an inner diameter of about 1.59 cm so that it slips onto the upper end 42 of the shaft 38 and rests on the annular shoulder 47 formed thereon. The annular weight 48 can be made from stainless steel or from other suitable materials resistant to corrosion in the presence of the test solution, which is 0.9 weight percent sodium chloride solution in distilled water. The combined weight of the piston 36 and annular weight 48 equals approximately 596 grams (g), which corresponds to a pressure applied to the sample 68 of about 0.3 pounds per square inch (psi), or about 20.7 dynes/cm$^2$ (2.07 kPa), over a sample area of about 28.27 cm$^2$.

When the test solution flows through the test apparatus during testing as described below, the sample container 30 generally rests on a 16 mesh rigid stainless steel support screen (not shown). Alternatively, the sample container 30 may rest on a support ring (not shown) diametrically sized substantially the same as the cylinder 34 so that the support ring does not restrict flow from the bottom of the container.

To conduct the Gel Bed Permeability Test under "free swell" conditions, the piston 36, with the weight 48 seated thereon, is placed in an empty sample container 30 and the height is measured using a suitable gauge accurate to 0.01 mm with the platen removed. It is important to measure the height of each sample container 30 empty and to keep track of which piston 36 and weight 48 is used when using multiple test apparatus. The same piston 36 and weight 48 should be used for measurement when the sample 68 is later swollen following saturation.

The sample to be tested is prepared from particles which are prescreened through a U.S. standard 30 mesh screen and retained on a U.S. standard 50 mesh screen. As a result, the test sample comprises particles sized in the range of about 300 to about 600 microns. The particles can be prescreened by hand or automatically. Also test samples can be as-is particles. Approximately 0.9 grams of the sample is placed in the sample container 30 and spread out evenly on the bottom of the sample container. The container, with 0.9 grams of sample in it, without the piston 36 and weight 48 therein, is then submerged in the test solution for a time period of about 60 minutes to saturate the sample and allow the sample to swell free of any restraining load.

At the end of this period, the piston 36 and weight 48 assembly is placed on the saturated sample 68 in the sample container 30 and then the sample container 30, piston 36, weight 48, and sample 68 are removed from the solution. The thickness of the saturated sample 68 is determined by again measuring the height from the bottom of the weight 48 to the top of the cylinder 34, using the same thickness gauge used previously provided that the zero point is unchanged from the initial height measurement. The height measurement obtained from measuring the empty sample container 30, piston 36, and weight 48 is subtracted from the height measurement obtained after saturating the sample 68. The resulting value is the thickness, or height "H" of the swollen sample.

The permeability measurement is initiated by delivering a flow of the test solution into the sample container 30 with the saturated sample 68, piston 36, and weight 48 inside. The flow rate of test solution into the container is adjusted to maintain a fluid height of about 7.8 cm above the bottom of the sample container. The quantity of solution passing through the sample 68 versus time is measured gravimetrically. Data points are collected every second for at least twenty seconds once the fluid level has been stabilized to and maintained at about 7.8 cm in height. The flow rate Q through the swollen sample 68 is determined in units of grams/second (g/s) by a linear least-square fit of fluid passing through the sample 68 (in grams) versus time (in seconds).

Permeability in cm$^2$ is obtained by the following equation:

$$K=[Q*H*\mu]/[A*\rho*P]$$

where K=Permeability (cm$^2$), Q=flow rate (g/sec), H=height of sample (cm), μ=liquid viscosity (poise) (approximately one centipoises for the test solution used with this Test), A=cross-sectional area for liquid flow (cm$^2$), ρ=liquid density (g/cm$^3$) (approximately one g/cm$^3$, for the test solution used with this Test) and P=hydrostatic pressure (dynes/cm$^2$) (normally approximately 3,923 dynes/cm$^2$). The hydrostatic pressure is calculated from $$P=\rho*g*h$$

where ρ=liquid density (g/cm$^3$), g=gravitational acceleration, nominally 981 cm/sec$^2$, and h=fluid height, e.g., 7.8 cm for the Gel Bed Permeability Test described herein.

A minimum of three samples is tested and the results are averaged to determine the gel bed permeability of the sample.

Gel Bed Permeability (GBP) Under 0.3 Psi Swell Pressure Test

As used herein, the Gel Bed Permeability (GBP) Under Load Test, otherwise referred to herein as GBP under 0.3 psi swell pressure, determines the permeability of a swollen bed of gel particles (e.g., the superabsorbent material or the absorbent material as those terms are used herein), under conditions that are commonly referred to as being "under load" conditions. The term "under load" means that swelling of the particles is restrained by a load generally consistent with normal usage loads applied to the particles, such as sitting, walking, twisting, etc. by the wearer.

More particularly, the Gel Bed Permeability Under Load Test is substantially the same as the Free Swell Gel Bed Permeability Test set forth previously with the following exception. After approximately 0.9 grams of the sample is placed in the sample container 30 and spread out evenly on the bottom of the sample container, the piston 36 and weight 48 are placed on the sample within the sample container prior to the sample container (with the piston and weight therein) being submerged in the test solution (0.9 wt % NaCl saline) for a time period of about 60 minutes. As a result, a 0.3 psi restraining load is applied to the sample as the sample becomes saturated and swells.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent composition comprising a biodegradable absorbent polymer and a surface modifying agent comprising a self-crosslinking hydrophilic soft polymer, wherein said biodegradable absorbent polymer is a superabsorbent material, wherein said hydrophilic soft polymer is a cationic polymer, and wherein said hydrophilic soft polymer comprises an alkoxysilane functionality.

2. The absorbent composition of claim 1 wherein said biodegradable absorbent polymer is selected from the group consisting of polysaccharide and poly amino acids.

3. The absorbent composition of claim 1 wherein said superabsorbent material is selected from the group consisting of polycarboxy polysaccharide and carboxymethyl cellulose.

4. The absorbent composition of claim 1 wherein said cationic polymer comprises functional groups selected from the group consisting of primary, secondary, and tertiary amine, imine, quaternary ammonium, and combinations thereof.

5. The absorbent composition of claim 1 wherein said cationic polymer is selected from the group consisting of salts of polyvinyl amine, polydiallyl dimethyl ammonium acryloyloxyethyl-trialkyl-substituted ammonium, acryloyloxypropyl-trialkyl-substituted ammonium, acrylamidoethyl-trialkyl-substituted ammonium, acrylamidopropyl-trialkyl-substituted ammonium and copolymers and mixtures thereof.

6. The absorbent composition of claim 1 wherein said cationic polymer includes about 0.1 to about 20-percent by mass ester units which include said alkoxysilane functionality.

7. The absorbent composition of claim 6 wherein said ester units are selected from the group consisting of acrylate ester, methacrylate ester, and combinations thereof.

8. The absorbent composition of claim 6 wherein said alkoxysilane functionality forms a silanol group upon exposure to water.

9. The absorbent composition of claim 8 wherein said silanol group condenses to form a crosslinked polymer upon exposure to water.

10. The absorbent composition of claim 1 having an AUL under 0.3 psi load value of 20 g/g or greater and a GBP under 0 psi swell pressure value of about $300 \times 10^{-9}$ cm$^2$ or greater.

11. The absorbent composition of claim 1 having an AUL under 0.3 psi load value of 20 g/g or greater and a GBP under 0.3 psi swell pressure value of about $20 \times 10^{-9}$ cm$^2$ or greater.

12. The absorbent composition of claim 11 further having a GBP under 0 psi swell pressure value of about $100 \times 10^{-9}$ cm$^2$ or greater.

13. The absorbent composition of claim 1 comprising said hydrophilic soft polymer in the amount of about 5-percent to about 15-percent by weight of said superabsorbent material.

14. An absorbent core comprising the absorbent composition of claim 1.

15. An absorbent article comprising the absorbent composition of claim 1.

* * * * *